United States Patent [19]
Nikitin et al.

[11] Patent Number: 5,633,492
[45] Date of Patent: May 27, 1997

[54] REAL TIME MONITORING OF CHANGES IN OBJECTS OR MEDIA

[75] Inventors: Petr Nikitin; Anatolii Beloglazov, both of Moscow, Russian Federation

[73] Assignee: Ceram Optec Industries, Inc., East Longmeadow, Mass.

[21] Appl. No.: 422,805

[22] Filed: Apr. 17, 1995

[51] Int. Cl.[6] .............................. H01J 40/14; G01J 1/04; G02B 6/00
[52] U.S. Cl. ..................... 250/214 R; 250/227.14; 385/141
[58] Field of Search .................. 250/227.14, 231.1, 250/214 R, 214.1; 356/36, 445; 359/350; 385/141

[56] References Cited

U.S. PATENT DOCUMENTS 4,565,422 1/1986 Seymour et al. ............. 385/36
4,765,705 8/1988 Seymour et al. ............. 359/566

OTHER PUBLICATIONS

B. Moslehi; M.W. Foster, & P. Harvey, "Optical Magnetic and Electric Field Sensors Based on Surface Plasmon Polariton Resonant Coupling" Electron-Lett. 27, 951-3 (1991).

Primary Examiner—Stephone Allen
Attorney, Agent, or Firm—Bolesh J. Skutnik

[57] ABSTRACT

The invention relates to non-contact methods of examining parameters of external actions on various media or objects. Such an action could be of various types, e.g., physical (pressure, heating, electric or magnetic field etc.), chemical (action of various chemical substances and associated reactions: binding, replacement, catalysis etc.), biological (action of microorganisms or viruses on a nutrient medium). The invention can be used in scientific research, technology and environmental monitoring.

18 Claims, 4 Drawing Sheets

REAL TIME MONITORING OF CHANGES IN OBJECTS OR MEDIA

BACKGROUND OF THE INVENTION

1. Field of the Invention

The invention relates to non-contact methods of examining parameters of external actions on various media or objects. Such an action could be of various types, e.g., physical (pressure, heating, electric or magnetic field etc.), chemical (action of various chemical substances and associated reactions: binding, replacement, catalysis etc.), biological (action of microorganisms or viruses on a nutrient medium). The invention could be used in scientific research, technology and environmental monitoring.

2. Information Disclosure Statement

The known method to measure parameters of an external action on a medium or an object, which is most closely analogous to the proposed one, comprises specification of reference relationships between a response signal and the external action on a sensitive medium, action by electromagnetic radiation on one of the sides of a structure made of a metal film deposited on a substrate, said medium being placed from the side of the metal film with respect to said structure, excitation of a surface electromagnetic wave (SEW) in the metal film, and generation of a response signal from said structure, one judging the parameters measured from comparison of said signal with the reference relationships [B.Moslehi, M. W. Foster and P. Harvey, "Optical magnetic and electric field sensors based on surface plasmon polariton resonant coupling". Electron. Lett., 27 (1991) 951–953]. The value of the measured parameter of an external action is obtained from recording the position of the resonance maximum of a SEW excitation efficiency or relative value of the SEW excitation efficiency within the slope of the resonance.

The associated apparatus for measuring parameters of an external action on medium or an object, which is most closely analogous to the proposed one, comprises an electromagnetic radiation source, a solid structure including a metal film serving for exciting a SEW in it, deposited on a substrate, and an information processing unit [B.Moslehi, M. W.Foster and P. Harvey].

The advantage of the mentioned method and the apparatus is a non-contact character of measurement accompanied with high accuracy. This enables one to solve a wide range of problems for examining various types of an external action on various media or objects. However, the response signal is here a purely optical signal resulting from changing parameters of a radiation beam reflected from the metal film under conditions of resonant SEW excitation in the film. To record a response signal associated with the reflected radiation beam, there is a need for a registration channel including an optical arrangement with a photodetector unit. This makes an overall device rather cumbersome, complicated and expensive and restricts the device's capabilities (particularly, its accuracy and its resolution limit), especially, when using an adjustable optical arrangement. Using a fixed one limits the dynamic range of measurements and the area of possible applications. These are significant intrinsic drawbacks of the mentioned method and the associated apparatus.

OBJECTS AND SUMMARY OF THE INVENTION

An object of the proposed invention is to provide a method and apparatus which improves accuracy and resolution limit of the measurements, extends the range of measured parameters and the area of possible applications.

Another object of the invention is to provide convenient, fast and inexpensive monitoring through utilizing of compact and inexpensive measuring tools which could be batch-fabricated on the base of conventional microelectronics technologies.

The above, and other objects, features and advantages of the present invitation will become apparent from the following description read in conjunction with the accompanying drawings.

DESCRIPTION OF PREFERRED EMBODIMENTS

Figure 1:
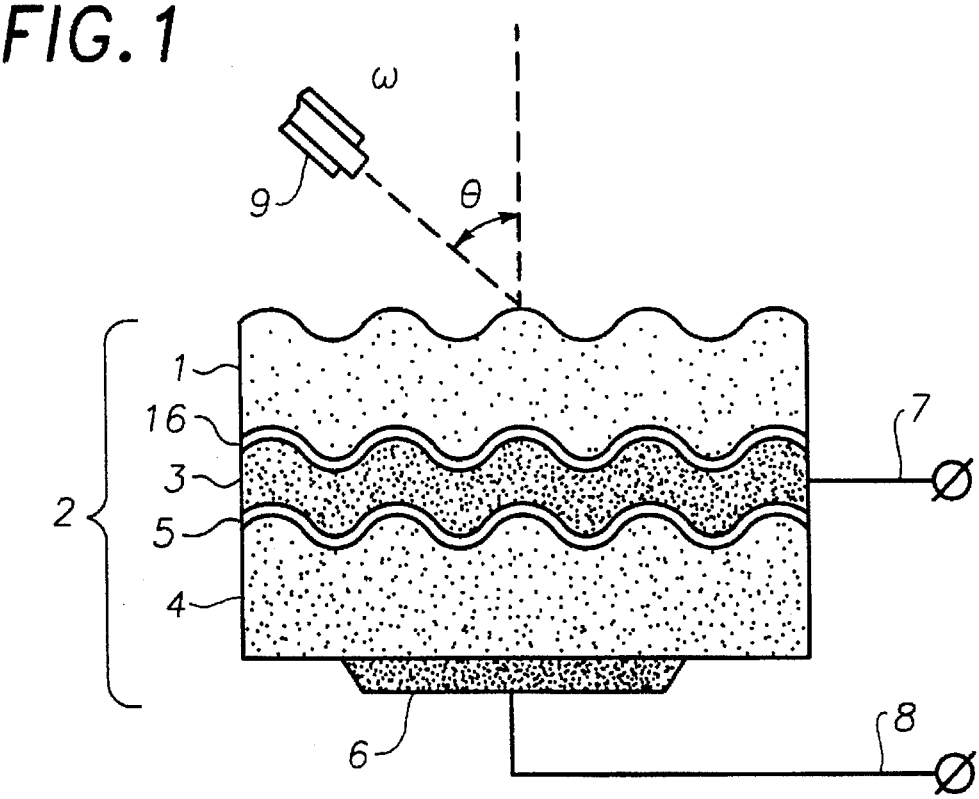
FIG. 1 illustrates a proposed method when a sensitive medium is situated in the regions of propagation of both radiation and SEW.

To achieve this goal in the proposed method, a semiconductor is used as the substrate on which the metal film is deposited immediately or via an interface layer to form the structure. An electric signal which is used as the response signal from the said structure is supplied to a circuit connected to the metal film and the semiconductor.

The electric signal is recorded within the slope of the resonant dependence of the signal value on, at least, one of the direction coordinates and/or the frequency of the electromagnetic radiation. The radiation beam used may be collimated, or divergent, or convergent, as well as monochromatic or non-monochromatic. It may also be linearly polarized and may be delivered directly or through an optical fiber. To extend the dynamic range of measurements, one varies an angular coordinate of the direction of the radiation beam relative to the structure or the radiation frequency.

To achieve the object of the invention in the associated apparatus, the substrate is made of a semiconductor, and the inputs of the information processing unit are in connection with the metal film and the substrate. The metal film and the semiconductor substrate are combined in a solid structure with or without an intermediate layer between them, for example, that with resistivity greater than that of the metal. In both cases, the interface(s) may be spatially modulated fully or partially.

The electromagnetic radiation source may be capable of changing a radiation frequency and/or direction of propagation relative to the said solid structure.

To excite SEW in the metal film, the surface of the metal film, opposite to the semiconductor, may be spatially modulated, or the apparatus is equipped with a component (e.g., a prism) which ensures total internal reflection of the radiation from its output side. There may be a gap between the output side of the component and the surface of the metal film, in which a layer of a substance is placed, refraction index of which is less than that of a medium of the component.

In addition, the apparatus may be provided with a radiation polarizer and/or an optical fiber to supply the radiation.

It should be emphasized that, in the proposed method and the apparatus, a SEW is excited in the metal film on the semiconductor substrate and the electric signal coming immediately from the metal and the semiconductor is recorded, which corresponds to examined parameters of an external action. Hence the one solid structure comprises, in this case, both the sensitive element of a measuring device and a photodetector, avoiding registration of the parameters of a reflected radiation beam. Consequently, there is no additional channel for recording any optical signal in contrast to the method of the prior art which caused the drawbacks mentioned above. The whole proposed apparatus (excluding an information processing unit) is simply an optoelectronic pair—a hybrid circuit which parts could be made by microelectronics industry. Thus, the present invention has apparent advantages over the known ones by providing a simpler and cheaper technique of measurement over a wide range of parameters, extending the area of possible applications and improving the accuracy and resolution of measurements through utilizing tools which are compact, cheap and batch-fabricated based of conventional microelectronics technologies.

Figure 2:
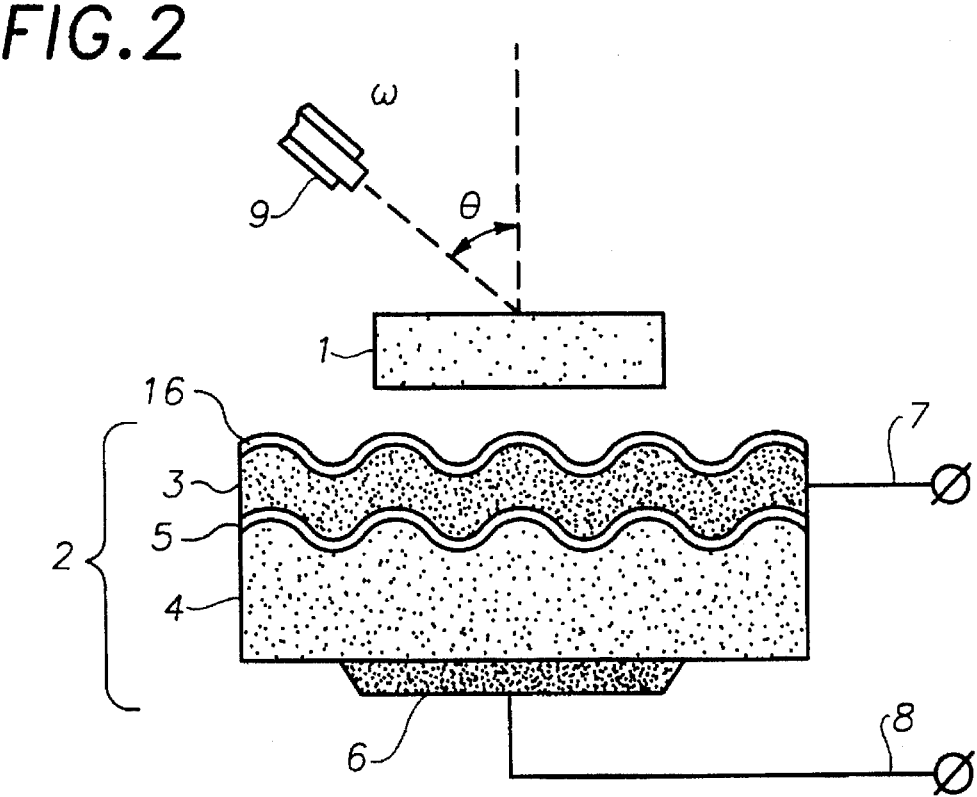
FIG. 2 illustrates a proposed method when a sensitive medium is situated in the region of propagation of radiation and outside that of SEW.

The invention is pictured in FIGS. 1–7. FIGS. 1, 2 illustrate the proposed method. In FIG. 1, a sensitive medium is situated in the regions of propagation of both radiation and SEW, while in FIG. 2 it is in the region of propagation of radiation and outside that of SEW.

Figure 3:
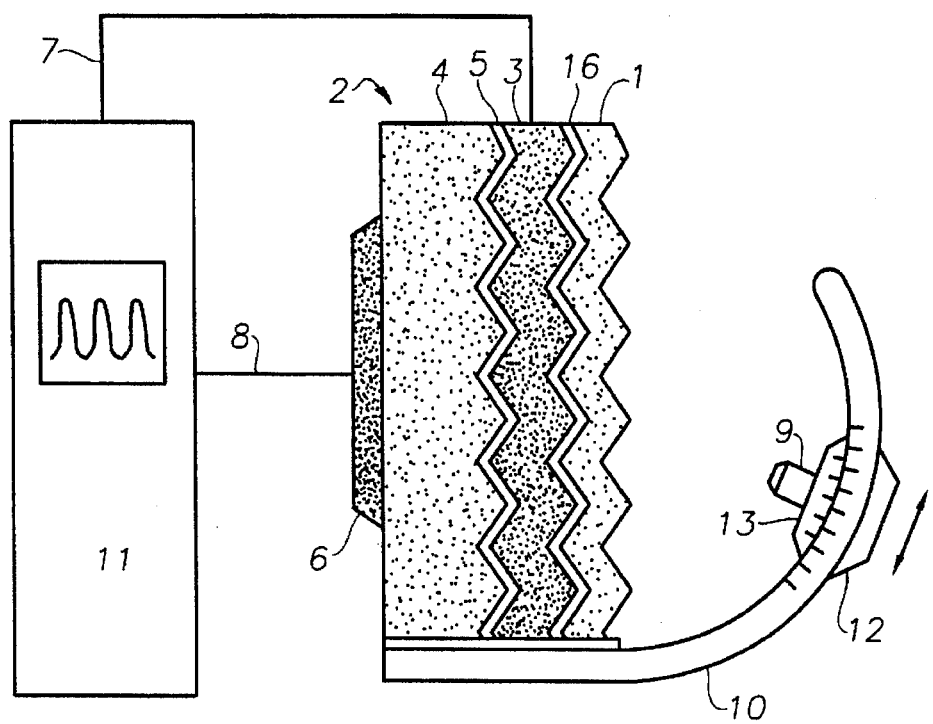
FIG. 3 shows a schematic view of the proposed apparatus based on the grating technique of SEW excitation when a sensitive medium is located in the region of SEW propagation.
Figure 4:
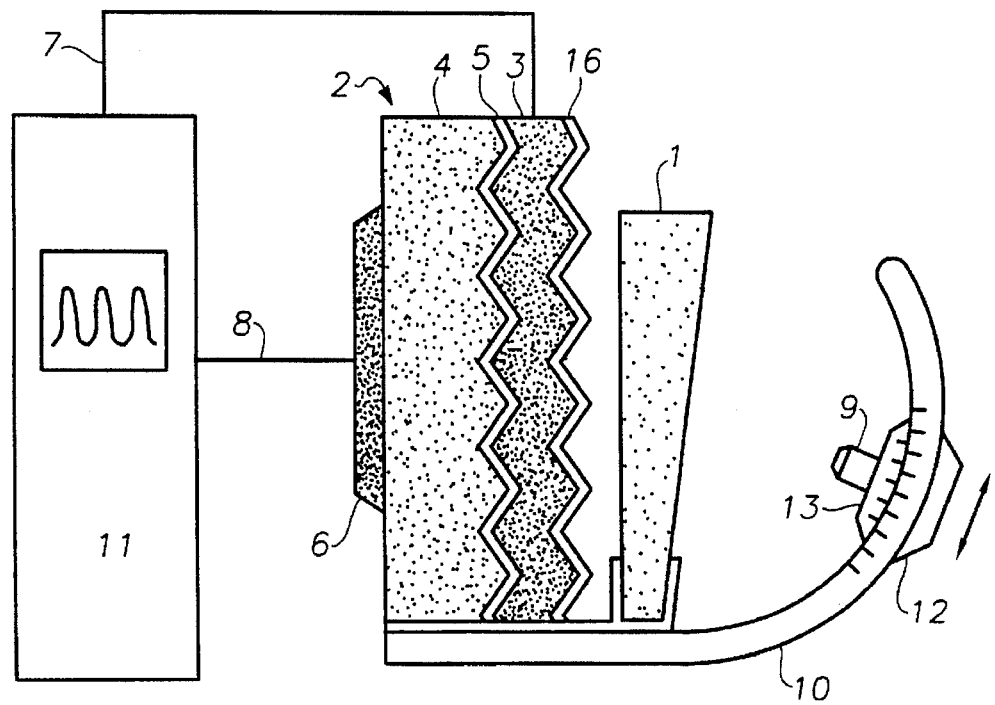
FIG. 4 shows a schematic view of the proposed apparatus based on the grating technique of SEW excitation in the case when a sensitive medium is located outside of the region of SEW propagation.
Figure 5:
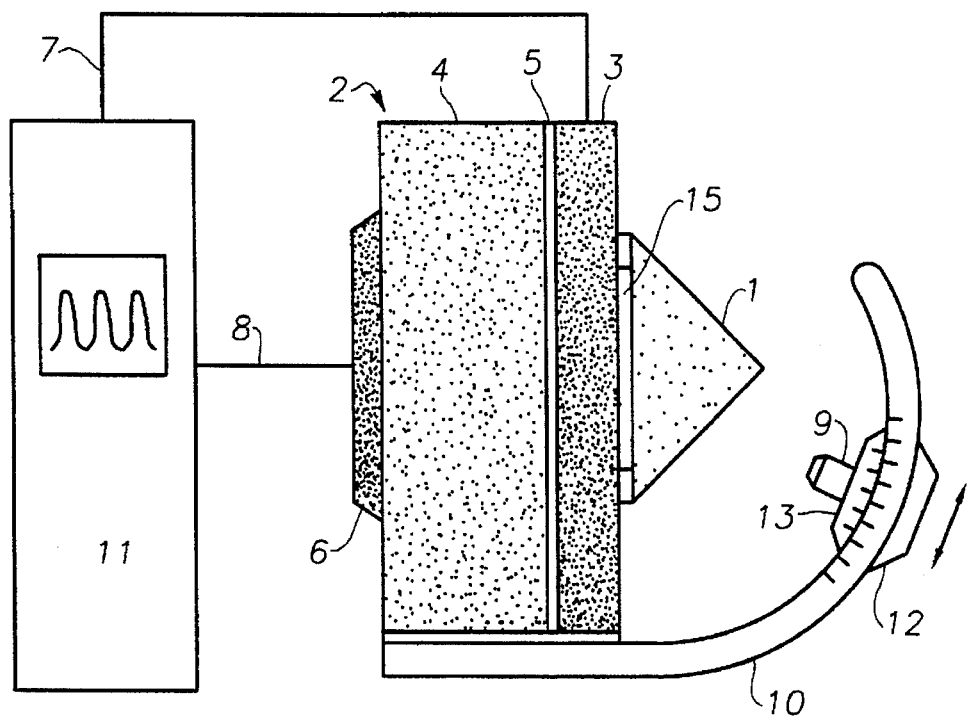
FIG. 5 illustrates the case when SEW is excited by means of attenuated total internal reflection from the output side of a prism.
Figure 6:
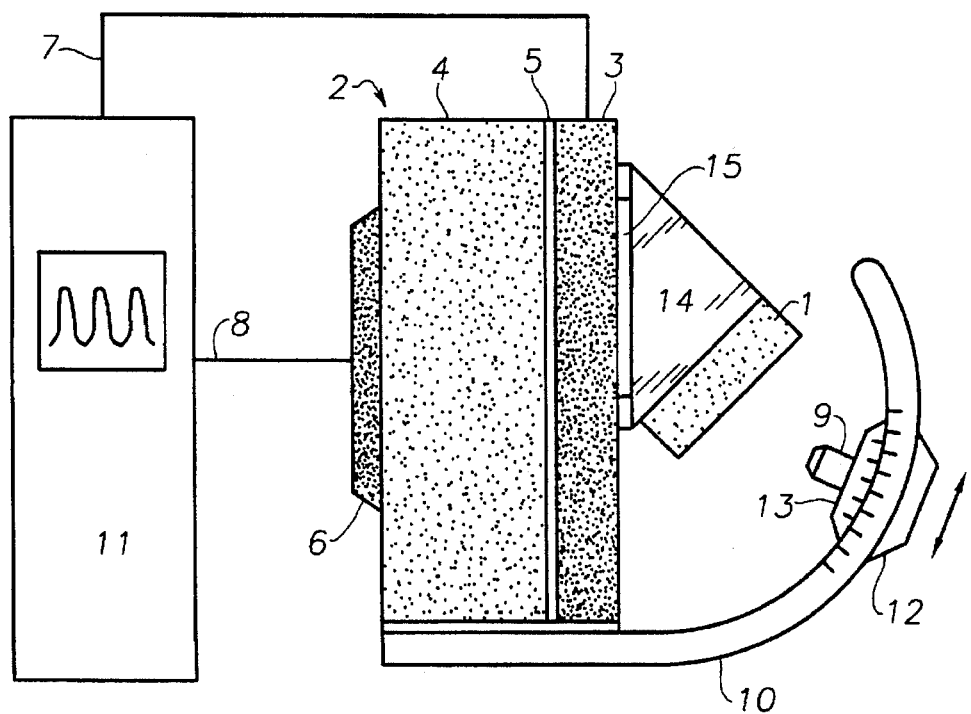
FIG. 6 shows the case when a radiation passes through a sensitive medium that is located outside the SEW region.

FIGS. 3–6 show the different variants of the schematic of the proposed apparatus. In FIGS. 3, 4, the variants of the apparatus based on the grating technique of SEW excitation are depicted. In FIG. 3, a sensitive medium is located in the region of SEW propagation, while, in FIG. 4, being outside of it. In FIGS. 5, 6, SEW is excited by means of attenuated total internal reflection from the output side of a prism. In FIG. 5, such a prism is formed by a sensitive medium itself and, hence, the medium is in the SEW region. In FIG. 6, a sensitive medium is passed by radiation and located outside the SEW region.

Figure 7:
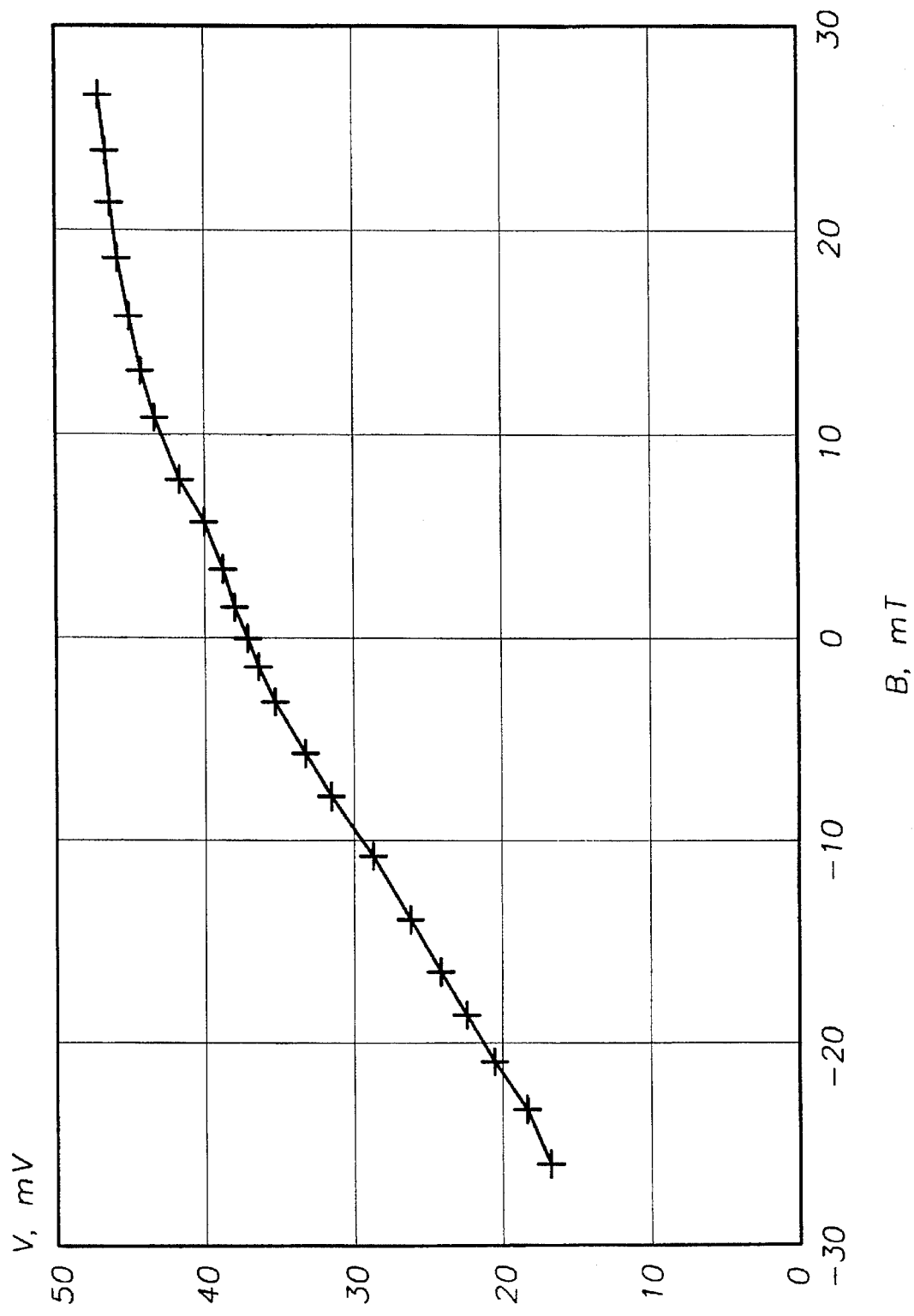
FIG. 7 shows an example of a reference relationship.

In FIG. 7, an example of a reference relationship is given.

The proposed method is based on having sensitive volume 1 experience the external action to be examined. The response of sensitive volume 1 to this action is a change in parameters of electromagnetic waves (SEW and/or radiation) propagating in it. The measure of such a change corresponds to the value of an examined action parameter in a known (specified) manner. Relevant examples are: a material varying its optical density (dielectric permittivity matrix) with mechanical tension or heating, an electrooptical material varying its dielectric permittivity matrix with an electric field, a magnetooptical material rotating a radiation polarization direction according to a magnetic field, etc. In this way, measuring parameters of an external action reduces to testing a proper specified sensitive volume.

To test sensitive volume 1, solid structure 2 is used, whose principal elements are metal film 3 (e.g., Ag, Au, Al, Cu) and semiconductor substrate 4 (e.g., Si, GaAs, InP). Sensitive volume 1 is located on the side of the metal film 3 facing away from structure 2 to ensure interaction of the sensitive volume 1 with the SEW at the surface of the film 3 and/or with radiation which excites the SEW. Structure 2 may include intermediate layer 5 (e.g. $SiO_2$) which is introduced, sometimes, between film 3 and substrate 4, in particular, to obtain a desirable resistance of the metal—semiconductor junction. The interface of metal 3 and semiconductor 4, or, at least, one of the surfaces of layer 5 may be spatially modulated (e.g., periodically rippled) to enhance scattering a SEW from metal 3 into semiconductor 4. Metal film 3 and substrate 4 with ohmic contact 6 are connected with electric outputs 7 and 8 respectively. Through them, structure 2 is connected to a measuring circuit as a photo element or a photodiode. A corresponding electric signal is recorded.

Electromagnetic radiation coming from source 9 (as a rule, visible or infrared) excites a SEW at a surface of film 3, nearer to sensitive volume 1. The excitation of the SEW is accompanied with resonant enhancement of the electric signal. Recording this signal and analyzing its peculiarities (e.g. value within the slope of the resonance or the angular or spectral position of the resonance) with reference relationships dependent on an investigated external action parameter (which governs some parameter of sensitive volume 1), one determines the value of the latter.

The following apparatus is put forward to realize the proposed method (FIGS. 3–6).

The apparatus is comprised of the following elements: measuring head 10 and information processing and indication unit 11 connected by wires 7 and 8.

The measuring head is made as an optoelectronic pair consisting of radiation source 9 and a detector.

As electromagnetic radiation source 9 (as a rule, visible or infrared), a built-in semiconductor light emitting device or the output end of an optical fiber is preferably to be used. This ensures the measuring head to be compact. Radiation source 9 may be frequency tunable and/or angle adjustable to scan the direction of radiation incidence with respect to structure 2. In FIGS. 3–6, the ability of angular scanning and taking readings is schematically shown by angular scale 12 with auxiliary scale 13. By frequency tuning and angular scanning of radiation source 9, one can adjust the apparatus and obtain reference relationships. Instead of angular scales, an angular position potentiometer detector is preferable. It converts directly readings of angular position of source 9 to an electric signal. Near the output of source 9, there may be a polarizer and/or a set of lenses (not shown). Correspondingly, a potentiometer detector of polarizer angular position is appropriate for use to investigate a polarization—dependent signal.

The above described solid structure 2 serves as a radiation detector.

To excite a SEW on the surface of metal film 3 opposite to semiconductor 4 with a grating technique, this surface is spatially modulated, e.g., in the form of a sine-like grating (FIGS. 3, 4). To excite a SEW with a technique of attenuated total internal reflection, prism is used in the schemes of FIGS. 5 and 6, which is rigidly bound with structure 2 forming gap 15 between them, according to the standard Otto technique for SEW excitation. Gap 15 is filled with air or another dielectric medium whose refraction index is less than that of prism 14. The arrangement in FIG. 5 is also based on the Otto technique where a wedge layer of sensitive volume 1 permeated by a radiation beam serves as a prism, having a refraction index greater than that of a substance in the gap 15.

The apparatus operates as follows. In the schemes of FIGS. 4, 6, a change in specified sensitive volume 1 which experiences the examined external action causes a change in the direction of incidence of radiation upon structure 2 or in the polarization direction of this radiation. In the schemes of FIGS. 3, 5, in addition, the examined action results in variation of a SEW wave vector value. Any of these reasons leads to a variation of a signal taken from measuring head 10, in accordance with the external action.

The method is based on fie following physical mechanism.

It is known, that a SEW at a media interface, particularly, of a metal (e.g. film 3) and a dielectric (e.g. sensitive volume 1) can be excited via coupling an incident p-polarized electromagnetic radiation coming from source 9 by means of a prism $$kn_{prism}\sin\theta = k_{SEW} \quad (1),$$

or a grating on metal film 3 surface:

$$kn\sin\theta + mG = k_{SEW} \quad (2)$$

The designations are:
$k = \omega/c = 2\pi/\lambda$ is an incident light wave vector of a wavelength $\lambda$ in vacuum,
n—a refraction index of tested sensitive volume 1,
$kn_{prism}$—a refraction index of the prism,
$\theta$—angle of radiation incidence onto the grating or the output side of the prism ($0<\theta<90°$),
m—positive or negative integer,
$G = 2\pi/\Lambda$—a reciprocal lattice vector of the grating with a period $\Lambda$.

$$k_{SEW} = \pm(2\pi/\lambda)[\epsilon'_{Mc}n^2/(\epsilon'_{Mc}+n^2)]^{1/2} \quad (3),$$

where "+" relates to m>0, "−" does to m<0, is a SEW wave vector. Here $\epsilon'_{Mc} = \text{Re}(\epsilon_{Mc})$ is a real part of a metal permittivity at the light frequency $\omega$ ($\epsilon'_{Mc}<0$, $|\epsilon'_{Mc}|>n^2$).

Relations (1) and (2) describe the position of the resonant maximum of the coupling efficiency (part of the energy of radiation transformed into that of SEW), dependent on k, n and $\theta$. When one of these parameters is allowed to change (e.g., n) the resonance position is changed (resonant k and $\theta$). When the parameter is changed within the slope of the resonant curve the coupling efficiency changes dramatically. In this connection, there follows a method of determining n of sensitive volume 1 adjacent to film 3 and, on its base, a method of measuring parameters of an external action on sensitive volume 1, exhibited by varying n, as well.

For one thing, n of sensitive volume 1 and, accordingly, the value of an external action parameter can be determined through measuring values of $\theta$ and $\omega$ corresponding to the resonance of the efficiency of radiation coupling to SEW at sensitive volume 1—metal 3 interface. Then, from calculated or experimental reference relationships between resonance values of $\theta(\omega)$ and the parameter of an external action on sensitive volume 1, one can find the value of the latter.

For another thing, one can fix $\theta$ and $\omega$ corresponding to the slope or the resonance curve of the coupling efficiency for the medium with a known $n=n_0$ and, accordingly, with a known (initial) value of the external action on it. The measurements of the parameters of this action are to be taken with respect to this initial value through measuring the difference of the respective values of the coupling efficiency within the slope of the resonance curve and comparing it with the proper reference relationship.

From a practical standpoint, it is more convenient to measure not the coupling efficiency itself but some signal dependent on it.

Such a signal is very easy to obtain when metal film 3 is combined with substrate 4 made of a semiconductor. In this case, the radiation to SEW coupling efficiency governs the value of the electric signal taken from outputs 7 and 8 connected immediately to film 3 and substrate 4. Film 3 and substrate 4 form structure 2 which is analogous to a traditional Schottky photodetector. As the latter, structure 2 can be connected up as a photoelement or a photodiode. The distinctive property of structure 2 is that the signal taken from it has a resonant maximum under the conditions of SEW excitation at the medium—metal interface.

There may be a different character of the relation between the SEW and the electric signal depending on specific operating mechanism.

A mechanism discussed in [S. R. J.Brueck, V.Diadiuk, T.Jones and W.Lenth. "Enhanced quantum efficiency internal photoemission detectors by grating coupling to surface plasma waves". Applied Physics Letters, 46 (1985) 915–917] was based on absorption of the SEW in the metal film, generation of hot charge carriers in it and emission of them into the semiconductor through the Schottky barrier. Such carriers were affected by the barrier electric field in the semiconductor and resulted in the electric response signal taken from the structure. The energy of the radiation quantum was less than the energy gap of the semiconductor. It was mentioned that, under this condition, the radiation to excite the SEW could be supplied to the metal film both through the air and through the semiconductor.

When the energy of the radiation quantum is greater than the energy gap of the semiconductor, electron—hole pairs in the semiconductor can be produced, resulting from the penetration of the SEW into the semiconductor and/or from reconversion of the SEW to a radiation at the metal—semiconductor interface and absorption of this radiation in the semiconductor. Electron—hole pairs are separated by the Schottky barrier field and result in a photoresponse. It is obvious that, in this case, the radiation to excite the SEW can be supplied only from the side opposite to the semiconductor.

Thus, one can determine the parameter of an external action on sensitive volume 1 through measuring the position of the resonance maximum of a photosignal taken from structure 2 combining metal 3 and semiconductor 4 under SEW excitation conditions and comparing this position with the reference one in the dependence on the radiation direction angular coordinate relative to structure 2 or on the radiation frequency. Within the slope of the resonance curve, another regime is preferable. When radiation direction or frequency is fixed within the slope of the correspondent resonant dependence of the photosignal, the structure operates as an immediate converter of the parameter of an external action to the photosignal. Consequently, measuring the photosignal and comparing it with the predetermined dependence of it on this parameter enables one to find the value of the latter. In this regime, the sensitivity to the external action is proportional to the steepness of the slope. The dynamic range of measured value of the action parameter is, in contrast, proportional to the width of the resonant curve. The width is contributed by a radiation divergence and a spectral bandwidth of radiation source 9. Apparently, to achieve a maximum sensitivity one should use monochromatic and collimated radiation. To extend the dynamic range, a divergent (convergent) or spectrum-broadened radiation can be used.

Within the scope of the concept discussed, an optically anisotropic sensitive volume 1 can be used as well. In this case, the measurement conditions are to be chosen in such a way that components of the dielectric matrix which are responsible for the propagation through sensitive volume 1 of a SEW and a radiation having proper polarization direction are affected by the external action.

To measure parameters of an external action on sensitive volume 1, tested sensitive volume 1 and film 3 are not obligatory to be in contact. On the surface of metal film 3, there may be auxiliary layer 16 (FIGS. 1–4) which serves to improve adhesion, to protect the film 3 from possible chemical attacks, etc. The SEW wave vector in such a multilayer system cannot be described by the simple expression (3). The dependence of $k_{sew}$ on n and, correspondingly, on the external action is still takes place, weakening as the thickness of layer 16 increases.

Sensitive volume 1 is not obligatory to be bound with structure 2. The properties of sensitive volume 1 which is apart from structure 2 at a distance exceeding a SEW penetration depth and is subjected to an external action can influence on SEW excitation through the direction of passing radiation. If the refraction index before and after the layer of sensitive volume 1 passed by the radiation is the same the layer should, apparently, to be a wedge.

In all the cases, the above discussed concept of the proposed method and apparatus holds on.

The proposed principle of measurements can be based on the dependence of the photosignal which is a response to SEW excitation not only on the refraction index but on the polarization properties of sensitive volume 1 as well, providing these properties are varying in a specified manner under the external action. If the value of polarization rotation of the radiation when passing sensitive volume 1 depends on the measured parameter of an external action (e.g., Faraday rotation of a polarization plane in a magnetic field), the polarization component that contributes to SEW and hence the signal value depend on the measured parameter, too. This dependence, in contrast with refraction—based ones, is not resonant but has the form $\sim\cos^2(\phi-\phi_0)$ where $\phi$ is the value of polarization rotation angle. To record such a dependence, linearly polarized radiation is needed.

The proposed method has been applied as follows. The value of the longitudinal component of the magnetic field produced by a coil was measured according to the scheme of FIG. 2. A semimagnetic semiconductor $Cd_{0.55}Mn_{0.45}Te$ with a giant Faraday rotation served as sensitive volume 1. A 5.8 mm thick slab of it was placed inside the coil perpendicular to the axis of the latter. The pre- polarized laser beam of a wavelength 0.63 µm passing through the slab along the axis had a power 1.65 mW and a divergence 0.65°. A grated Ag/n-GaAs Schottky barrier photodetector with a she-like grating period of 0.46 µm was placed near the maximum of a photosignal resonance associated with SEW, polarization direction being at about 45° with respect to the plane of incidence. A reverse bias 1.4 V was applied to the phoodetector connected to a measuring scheme as a photodiode with a 40 kΩ load resistance. The coil was fed with a DC source. To obtain a reference relationship, a standard Hall teslameter was used. The relationship is given in FIG. 7. It is sine-like. When applying an unknown magnetic field, a signal V=40±0.1 mV was recorded. From the FIG. 7, we found the longitudinal field to be B=5.8±0.02 mT.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for measuring parameters of an external action on a medium or an object, which comprises the steps of:
    a. specifying a reference relationship between a response signal and an external action on a volume of a sensitive material;
    b. fabricating a composite structure which comprises a metal film deposited on a semiconducting substrate and said sensitive material is placed on a side of said metal film facing away from said semiconducting substrate;
    c. creating an electrical circuit in said composite structure between said metal film and said semiconducting substrate;
    d. illuminating said composite structure with electromagnetic radiation;
    e. exciting a surface electromagnetic wave in said metal film;
    f. creating a response signal in said composite structure as an electric signal which arises in a circuit between said semiconducting substrate and said metal film;
    g. measuring said response signal;
    h. comparing said response signal with said reference relationships to determine parameters of said external action acting on said sensitive material.

2. The method according to claim 1, having an additional step, within said fabrication step, of:
    introducing at least a partial spatial modulation into at least one surface of said metal film thereby enhancing said creation of a response signal.

3. The method according to claim 1, having an additional step, within said fabrication step, of:
    introducing an intermediate layer whose resistivity is greater than that of said metal film between said metal film and said semiconducting substrate.

4. The method according to claim 1, having an additional step, within said illumination step wherein said electromagnetic radiation has a propagation direction relative to said composite structure, of:
    varying an angular coordinate of said electromagnetic radiation's propagation direction relative to said composite structure.

5. The method according to claim 1, having an additional step, within said illumination step wherein said electromagnetic radiation has a frequency or a range of frequencies, of:
    varying said electromagnetic radiation's frequency.

6. The method according to claim 1, having an additional step, within said illumination step,
    providing said electromagnetic radiation as an energy beam, selected from the following; a divergent beam, a convergent beam, or a collimated beam.

7. The method according to claim 1, having an additional step, within said illumination step, of:
    providing said electromagnetic radiation as an energy beam, selected from the following; a monochromatic beam, a non-monochromatic beam, or a linearly polarized beam.

8. The method according to claim 1, where said illumination step is carried out by transmitting said electromagnetic radiation through an optical fiber onto said sensitive material.

9. The method according to claim 1, having an additional step of:

monitoring a derivative electrical signal which corresponds to a slope of a resonance curve defining a dependence of said response signal on at least one of said radiation's propagation direction coordinates or of said radiation's frequency.

10. A photodetection device for measuring parameters of an external action on a medium or on an object which comprises:

a source of electromagnetic radiation;

a composite structure comprising a metal film deposited on a semiconducting substrate such that in operating said device a surface electromagnetic wave is created in said metal film;

a volume of a material sensitive to said external action producing a modified electric signal in response to exposure to said external action;

said volume of sensitive material being in contact with said metal film on a surface facing away from said semiconducting substrate;

an information processing unit; and inputs of said information processing unit are connected one to said metal film and another to said semiconducting substrate.

11. A device according to claim 10, wherein at least one surface of said metal film has been at least partially, spatially modulated.

12. A device according to claim 10, which further comprises:

an intermediate layer between said metal film and said semiconducting substrate, said intermediate layer having a resistivity greater than that of said metal film.

13. A device according to claim 12, wherein at least one surface of said intermediate layer is at least partially spatially modulated.

14. A device according to claim 10, which further comprises:

a means to vary and select a frequency of said source of electromagnetic radiation.

15. A device according to claim 10, which further comprises:

said electromagnetic radiation has a propagation direction relative to said composite structure; and a means to change said propagation direction of said electromagnetic radiation relative to said composite structure.

16. A device according to claim 10, which further comprises:

a layer between said metal film and said sensitive material, creating an interface between said metal film and said sensitive material; and said layer having a refractive index lower than that of said sensitive material such that said electromagnetic radiation is totally internally reflected at said interface.

17. A device according to claim 10, which further comprises:

a means to polarize a beam of electromagnetic radiation propagating from said electromagnetic radiation source.

18. A device according to claim 10, wherein an optical fiber is said electromagnetic radiation source, transmitting electromagnetic radiation from a remote source.

* * * * *